(12) United States Patent
Leconte et al.

(10) Patent No.: US 9,746,424 B2
(45) Date of Patent: Aug. 29, 2017

(54) METHOD AND DEVICE FOR OBSERVING AND ANALYSING OPTICAL SINGULARITIES IN GLASS CONTAINERS

(71) Applicant: MSC & SGCC, Vourles (FR)

(72) Inventors: Marc Leconte, Loire sur Rhone (FR); Lubin Fayolle, Brignais (FR); Eric Pirot, Cesson-Sevigne (FR)

(73) Assignee: MSC & SGCC, Vourles (FR)

( * ) Notice: Subject to any disclaimer, the term of this patent is extended or adjusted under 35 U.S.C. 154(b) by 7 days.

(21) Appl. No.: 14/888,104

(22) PCT Filed: Apr. 30, 2014

(86) PCT No.: PCT/FR2014/051042
§ 371 (c)(1),
(2) Date: Oct. 30, 2015

(87) PCT Pub. No.: WO2014/177814
PCT Pub. Date: Nov. 6, 2014

(65) Prior Publication Data
US 2016/0077020 A1 Mar. 17, 2016

(30) Foreign Application Priority Data
May 3, 2013 (FR) ...................................... 13 54107

(51) Int. Cl.
*G01N 21/90* (2006.01)
*B07C 5/34* (2006.01)
*G01N 21/84* (2006.01)

(52) U.S. Cl.
CPC ....... *G01N 21/9036* (2013.01); *B07C 5/3408* (2013.01); *G01N 21/909* (2013.01); *G01N 2021/845* (2013.01)

(58) Field of Classification Search
CPC .. G01N 21/59; G01N 21/909; G01N 21/9054; G01N 21/9036; G01N 2201/0634; B07C 5/3408
(Continued)

(56) References Cited
U.S. PATENT DOCUMENTS

| 4,367,405 A | * | 1/1983 | Ford | ....................... B07C 5/126 209/526 |
| 4,424,441 A | * | 1/1984 | Bieringer | ................. G01V 8/12 250/223 B |

(Continued)

FOREIGN PATENT DOCUMENTS

FR 2 780 533 12/1999
FR 2 907 370 4/2008

*Primary Examiner* — Hoa Pham
(74) *Attorney, Agent, or Firm* — Clark & Brody (57) ABSTRACT

A method of observing and analyzing optical singularities includes illuminating an outside of a container by using a light-emitting surface of axial symmetry around a vertical axis (Z) parallel to the axes of symmetry of the containers, with a property of the emission that is detectable by the acquisition system(s) varying along a generator line of the light-emitting surface. For containers of low transmittance, taking the view image of the container portion by the image acquisition device receiving light beams comes from a portion of the light-emitting surface situated on the same side of the container. For containers of high transmittance, taking the view of the container portion by the image acquisition device receiving light beams comes from a portion of the light-emitting surface that is diametrically opposite relative to the container.

26 Claims, 6 Drawing Sheets

(58) Field of Classification Search
USPC ..... 356/240.1, 239.1, 239.4, 428; 250/223 B
See application file for complete search history.

(56) References Cited

U.S. PATENT DOCUMENTS

| | | | |
|---|---|---|---|
| 4,487,322 A | | 12/1984 | Juvinall |
| 4,610,542 A | | 9/1986 | Ringlien |
| 4,644,151 A | | 2/1987 | Juvinall |
| 5,072,127 A | * | 12/1991 | Cochran ............ G01N 21/8806 250/223 B |
| 6,031,221 A | * | 2/2000 | Furnas ............... G01N 21/9036 209/524 |
| 6,424,414 B1 | | 7/2002 | Weiland et al. |
| 6,620,352 B1 | * | 9/2003 | Davis ..................... B29C 49/78 264/40.4 |
| 2005/0174571 A1 | * | 8/2005 | Cochran ............ G01N 21/8806 356/240.1 |
| 2006/0126060 A1 | * | 6/2006 | Colle ................. G01N 21/9054 356/239.4 |
| 2006/0162472 A1 | * | 7/2006 | Schmidt ................ B07C 5/3408 73/865.8 |
| 2014/0160472 A1 | * | 6/2014 | Levesque ................ B07C 5/342 356/239.7 |

* cited by examiner

METHOD AND DEVICE FOR OBSERVING AND ANALYSING OPTICAL SINGULARITIES IN GLASS CONTAINERS

FIELD OF THE INVENTION

The invention relates to the technical field of observing and analyzing optical singularities carried by glass containers, such as bottles, pots, and flasks.

BACKGROUND ART

A few concepts of optical physics or mathematics are summarized below. In optics, the luminous exitance of a point of a light-emitting surface is the flux emitted into a half-space by unit area of the emissive surface centered at the point. This concept is sometimes also referred to as emittance or as radiance. A gradient is the derivative along one or more directions of a magnitude, in other words a gradient means that the magnitude varies. A luminous exitance gradient means that luminous exitance varies along the emitting surface. Likewise, a color gradient means that the color of the light emitted varies along the emitting surface. A diffuser is an element made of transparent or translucent material that diffuses light within its bulk and/or at its surface.

The term "singularities" is used to designate small portions of a container or of its surface that present properties that are different from the properties in their neighborhood on or in the container. Optical singularities thus designate portions of a container having optical properties that are different from the optical properties in their neighborhood on or in the container. Specifically, these optical singularities mainly present a refraction and/or reflection effect that is abnormal compared with their neighborhood. Refracting and/or reflecting defects, codes, or indeed decoration such as identification marks on the surfaces of containers thus constitute optical singularities that deflect light in a manner that differs compared with their neighborhood, either in terms of transmission (interfaces) or else in terms of specular reflection.

The term "view" is used to mean an image in the optical sense, i.e. a two-dimensional signal of gray levels or of colors obtained by projecting the container by means of an imaging optical device that is capable of "conjugation" in the optical sense. A camera having a lens can form at least one view. A camera can form a plurality of views simultaneously, e.g. by using a system of mirrors splitting its fields of view into N different views. These views are different if their viewpoints and observation directions are different. It is possible to associate a view with a magnification. In the present application, the term "image" is reserved for designating the signal produced by a camera, where such an image may contain a plurality of views.

Glass is a material that is transparent to visible light. Nevertheless, transmission at each wavelength depends on the tint of the glass and on the thickness passed through by the light in question. The transmittance of glass is measured as a ratio (in %) between the incident light and the transmitted light for a given thickness. It is even possible use a spectrometer to measure transmittance as a function of wavelength so as to obtain a transmission spectrum that characterizes the tint of the glass. For certain low transmittance tints, i.e. tints that are very dark or present a black appearance, and/or for certain thicknesses of glass (walls up to 5 millimeters (mm) thick) with little light passing through the wall of the container, it is possible to have transmittances of less than 1% for practically the entire visible spectrum.

The transparency of glass is a property that is in widespread use for performing optical inspections by making images in transmission of containers and by analyzing those images. The methods in most widespread use consist in backlighting containers using a uniform extended light source, and making images of the containers. Two known phenomena in the field of geometrical optics are used: absorption by so-called opaque defects or by differing optical transmission of the glass (a foreign body or extra thickness of tinted glass), and refraction of light by surface singularities such as cracks, tears, broken seeds, or missing material such as bubbles in the wall, or indeed inclusions of different optical index.

In order to improve the detection of so-called "refracting" defects by reinforcing their contrast in images, U.S. Pat. No. 4,487,322 proposes using a light source presenting a gradient of luminous exitance. Since they deflect light, defects are not illuminated by the same portion of the source as are their neighborhoods, and because of the gradient of luminous exitance in the source, they do not have the same perceived light level as their neighborhoods.

U.S. Pat. No. 6,424,414 describes a method and apparatus for detecting light-refracting defects that might be present in transparent containers. The apparatus described by that patent has a light source presenting a light gradient in a direction along the axis of the container. The light source is in alignment with a camera receiving the light passing through the container. Although such apparatus is suitable for detecting light-refracting defects in transmission, it is not suitable for acquiring images of the container in reflection, in particular for the purpose of analyzing marks or codes made on the surfaces of containers that present low or high transmittance.

For glass containers, it is known to etch a mold number code in molds in the form of beads. When the marks or codes such as mold numbers are made by molding, the portions in relief obtained on the containers are tall (extra thickness greater than >0.5 mm), and these portions in relief (referred to as "beads") present a size of millimeter order (diameter >0.8 mm).

It is known to read back mold numbers molded on containers by using devices that set each container into rotation and that illuminate the beads by means of directional and focused lightwaves (light beams that are narrow, small, with little or no divergence). Said light rays all having neighboring angles of incidence and they are reflected by the beads in a precise direction defined by the angles of incidence and by the angles of the beads. Sensors pick up the reflections and decode them. Such systems operate only on portions in relief that are of relatively large size and by putting the containers into rotation, which is expensive and disturbs manufacturing lines, which generally involve travel that is linear.

Patent FR 2 780 533 teaches a device using that optical method of reflecting onto the container focused light that has been emitted by a source, but that is adapted to reading in devices that convey containers in translation only, which is much faster and less expensive in use than systems involving rotation. The optical means are adapted to enable an image to be obtained of the entire code-carrying insweep, with the insweep appearing black and the code white. The focused incident light beams are converted to the periphery in the form of a light cone, and the rays reflected by the beads, and by the beads only, are taken by a conical mirror into the form of a plane image in an analysis device. Devices of that type are effective for codes presenting relatively large portions in relief, e.g. taller than 0.5 mm. It is necessary for the beads to have a surface area that is sufficient to be capable of returning a large amount of light in the single observation direction, while the rest of the incident light is reflected in any other direction by the background surface carrying said portions in relief.

In other words, those techniques with directional lighting and a predefined angle of observation work only for portions in relief that are tall, so that the direction in which light rays are reflected by the beads departs sufficiently from the direction of light rays that are reflected by the background surface. It should be observed that that type of system enables the light reflected by the portions in relief to be viewed as white marks compared with a (background) surface that remains black. Furthermore, the high contrast gives information that is practically binary, with beads being seen or not seen, with only bead portions being distinguished, but always at an intensity that is very strong compared with their neighborhoods. When portions in relief are small, e.g. because the molds are worn, the white areas corresponding to the beads in the image becomes small or even not observable.

U.S. Pat. No. 4,644,151 reuses conventional prior art but proposes using a camera having a source that is provided with a luminous exitance gradient in a direction parallel to the axis of rotation of the container. That system thus requires the container to be rotated, giving rise to the numerous drawbacks described above. It is not suitable for reading codes on traveling containers.

When the marks, e.g. in the form of a Datamatrix code, are made by laser on hot glass as described in patent FR 2 907 370, the portions in relief on the surface of glass containers are much smaller than with mold numbers, and in addition the code points are much smaller, having diameters of less than 0.3 mm. The solution consists in obtaining on a priority basis lighting that is uniform and in taking a series of matrix images of the wall of the container while it is rotating. The source is extended and uniform (without gaps), thereby providing the image with a uniform background, but it is of a size that is nevertheless limited in order to make a certain amount of contrast available. That system is thus suitable for marks of the Datamatrix type obtained by laser beam on containers while they are still hot, i.e. having portions in relief that are small. Nevertheless, that system requires the container to be rotated and it is not suitable for reading codes on traveling containers.

The present invention thus seeks to remedy the drawbacks of the prior art by proposing a novel optical technique for observing and analyzing optical singularities that may present only weak refracting power and that are carried by containers.

SUMMARY OF THE INVENTION

The invention seeks to provide a novel technique enabling optical singularities carried at the surface or in the wall of a container to be observed and analyzed, and making this possible regardless of the transmittance of the material constituting the container.

To achieve such an object, the present invention relates to an observation and analysis method for observing and analyzing optical singularities that deflect light and that are carried at the surface or in the wall of a container made of glass and possessing an axis of symmetry, the method consisting in:

illuminating the container by means of a diffuse light source presenting variation in a property of light along a variation direction;

placing at least one image acquisition device sensitive to said property of light and to its variation so as to take at least one view of a container portion that might contain optical singularities when observed from at least one viewpoint along an observation axis; and processing at least one view in order to analyze the optical singularities.

According to the invention, the method consists in:

illuminating the outside of the container by using a light-emitting surface of axial symmetry around a vertical axis parallel to the axis of symmetry of the containers, with the variation direction of the light property running along a generator line of the light-emitting surface at all points of the light-emitting surface;

with containers of low transmittance, taking the view of the container portion by the image acquisition device receiving light beams coming from a portion of the light-emitting surface of axial symmetry situated on the same side of the container as the viewpoint, which beams are reflected by the surface of the container in application of the laws of specular reflection; or with containers of high transmittance, taking the view of the container portion by the image acquisition device receiving light beams coming from a portion of the light-emitting surface of axial symmetry that is diametrically opposite from the viewpoint relative to the container, which beams have been transmitted through the walls of the container in application of the laws of refraction.

In addition, the method of the invention may further consist in combining at least and/or more of the following additional characteristics:

considering that containers have high transmittance when interfering spots appear in the image so as to interfere with the observation of optical singularities, where the spots are generated by interfering light rays propagating without attenuation through the wall, and in considering that containers are of low transmittance when said interfering light rays are absorbed by the tint of the material to such an extent as to avoid disturbing the analysis of optical singularities;

causing containers to travel, without rotating about their axes, along a travel direction perpendicular to and substantially intersecting the vertical axis of symmetry of the light-emitting surface of axial symmetry;

providing passages in two opposite sides of the light-emitting surface of axial symmetry for passing at least a portion of a traveling container;

taking a plurality of views of the portion of the container that might contain optical singularities along different observation axes that are distributed angularly around the vertical axis of the container so as to ensure that the periphery of the container is analyzed completely or even redundantly;

taking a plurality of views obtained by means of a combination of cameras and optical systems so that the number of cameras is less than or equal to the number of viewpoints and of observation directions;

pointing the observation axes upwards in order to analyze the optical singularities situated on the necks of the containers;

analyzing marks as optical singularities and in interpreting them in order to obtain information about the container or its fabrication for at least one operation selected from: sorting, tracing, identifying dating, and authenticating the container;

detecting and/or identifying optical singularities as defects of the containers;

when observing a container, different angular portions of the light-emitting surface of axial symmetry are illuminated separately and in succession while simultaneously acquiring views synchronously with the illumination of the angular portions, the views being taken from viewpoints that are opposite from or on the same side as said angular portions relative to the container;

illuminating with a diffuse light source in which the light property that varies along a generator line of the light-emitting surface of axial symmetry is the luminous exitance of the light-emitting surface;

the light property that varies along a generator line of the light-emitting surface of axial symmetry is the color of the emitted light; and the emission spectrum of the light source is adapted so as to increase or else reduce or even eliminate the energy of the light beams transmitted through the walls of the container.

The present invention also seeks to propose a technique that is suitable for operating with or without the containers being set into rotation. It thus makes it possible in particular to analyze optical singularities carried by containers that are traveling along a curvilinear path or more simply still that are traveling in pure translation along the travel direction.

The invention also proposes a device for observing and analyzing optical singularities that deflects light and that are carried at the surface of or in the wall of a glass container possessing an axis of symmetry, the device comprising:

a diffuse light source presenting variation of a property of light along a variation direction;

at least one image acquisition device for taking at least one view of a container portion that might contain optical singularities observed from at least one viewpoint along an observation axis; and means for processing at least one view in order to analyze the singularities.

According to the invention:

the light-emitting surface is positioned to illuminate the outside of the container, said surface being a surface of axial symmetry about a vertical axis parallel to the axes of symmetry of the containers, with the light property varying along a generator line of the light-emitting surface along the variation direction at all points of the light-emitting surface of axial symmetry;

for containers of low transmittance, the image acquisition device is suitable for taking the view of the container portion from a viewpoint in order to receive the light beams coming from a portion of the light-emitting surface of axial symmetry that is situated on the same side of the container as the viewpoint, which beams are reflected by the surface of the container; or for containers of high transmittance, the image acquisition device is suitable for taking the view of the container portion from a viewpoint for receiving light beams coming from a portion of the light-emitting surface of axial symmetry that is diametrically opposite from the viewpoint relative to the container, which beams are transmitted through the walls of the container.

Furthermore, the device of the invention may further present in combination at least one and/or more of the following additional characteristics:

the light-emitting surface of axial symmetry is a surface of revolution, e.g. a cylinder, a truncated cone, a hemisphere, or a disk;

the luminous exitance of the light-emitting surface of axial symmetry varies at all points of the light-emitting surface of axial symmetry along a generator line of said surface;

the color of the light emitted by the light-emitting surface of axial symmetry varies at all points of the light-emitting surface of axial symmetry along a generator line of said surface;

the light source includes at least one lighting ring illuminating the bottom or top end of a cylindrical or frustoconical diffuser;

the luminous source of axial symmetry includes a lighting ring illuminating a light diffusing hemisphere opposite from its equatorial plane, in a manner that varies as a function of the point under consideration of the diffuser, but with axial symmetry relative to the axis of the hemisphere;

the light source includes a plane diffuser disk illuminated at its center by a source or at its periphery by a lighting ring, in a manner that varies as a function of the point under consideration of the diffuser, but with axial symmetry relative to the axis of the disk;

the emission spectrum of the light source is adapted so as to increase or else reduce or even eliminate the energy of light beams transmitted through the walls of the container;

the light source includes a diffuser that is completely illuminated and against which there is placed on one side or the other a film of transmission that varies, at least for one wavelength, along a generator line of the light-emitting surface;

the light-emitting surface of axial symmetry has a plurality of angular sectors that are controlled to be switched on and/or off selectively;

the light-emitting surface of axial symmetry is provided with an entry passage and an exit passage for a portion of a container, which passages are arranged symmetrically about the vertical axis;

a series of image acquisition devices placed around the vertical axis in order to observe the container from a plurality of viewpoints enabling all or part of the periphery of the container to be observed; and the image acquisition devices are positioned with an observation axis pointing upwards at an angle lying in the range 3° to 10° relative to the horizontal.

BRIEF DESCRIPTION OF THE DRAWINGS

Various other characteristics appear from the following description made with reference to the accompanying drawings which show, as non-limiting examples, embodiments of the invention.

DETAILED DESCRIPTION OF THE INVENTION

Figure 1:
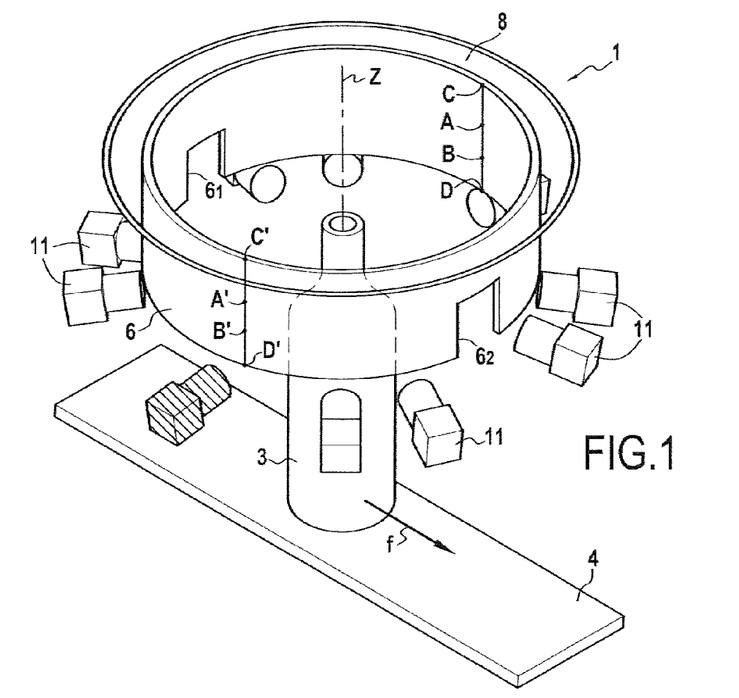
FIG. 1 is a perspective view of a first variant embodiment of an observation and analysis device in accordance with the invention, including a light-emitting surface presenting axial symmetry, and by way of example cylindrical type symmetry.
Figure 2:
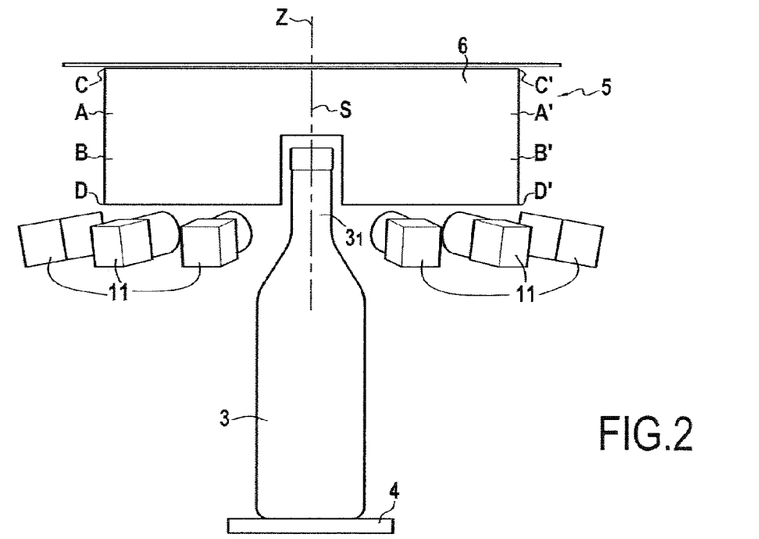
FIG. 2 is an elevation view of the observation and analysis device shown in FIG. 1.
Figure 3:
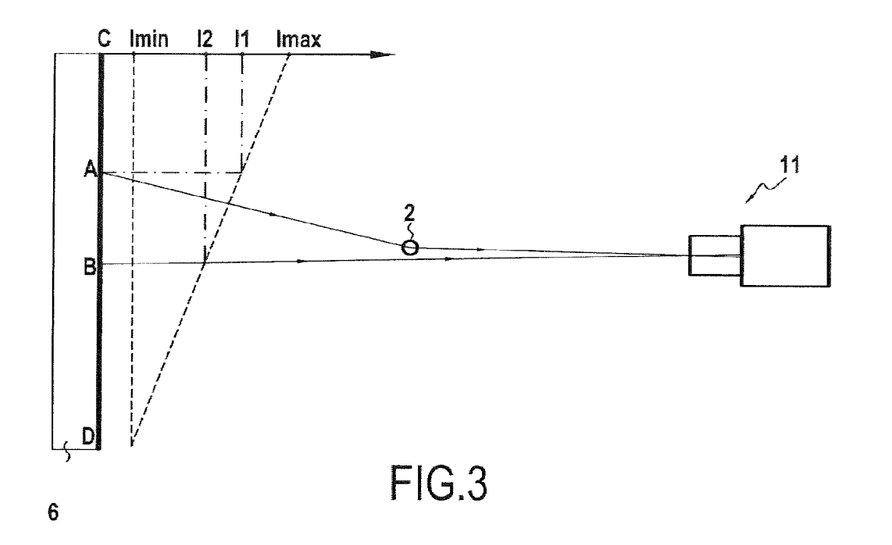
FIG. 3 is a theoretical diagram showing the path followed by light rays coming from a light source with a constant and non-zero luminous exitance gradient, as recovered by an image acquisition system.

As can be seen more clearly in FIGS. 1 to 3, the invention relates to a device 1 for observing and analyzing optical singularities 2 that deflect light, which singularities are located at the surface of or within the wall of a glass container 3 that presents an axis of symmetry S. In a preferred embodiment, the container 3 is caused to travel along a curvilinear path, or still more simply in translation along a travel direction represented by arrow f so as to enable it to be observed by the device 1. The containers 3 are thus moved for example by means of a conveyor 4 so as to travel in succession past the device 1.

In the embodiment shown in the drawings, the device 1 is particularly suitable for observing optical singularities in the necks $3_1$ of containers. Concerning optical singularities, provision may be made to observe and analyze a code, e.g. etched by means of a laser on the neck, or an identifying mark, or a pattern made by molding. Naturally, the device may be adapted to observe optical singularities located on other portions of containers, such as the insweep or the shoulder, for example. In another variant embodiment, the optical singularities are defects that need to be detected.

The device 1 comprises an extended and diffuse source of light 5 presenting a light-emitting surface 6 of axial symmetry about a vertical axis Z parallel to or coinciding with the axis of symmetry S of the containers 3. In accordance with the invention, the light-emitting surface 6 of axial symmetry presents, in a variation direction of said light-emitting surface, a gradient or variation in at least one property of its light, i.e. a magnitude that characterizes the light emitted and that is measurable by an image acquisition device, such as its color or its total emitted intensity, i.e. more precisely its luminous exitance, or indeed the length of time it is switched on in pulsed operation. This variation in at least one property of the light takes place at all points of the light-emitting surface along a curve defined by the intersection between the light-emitting surface and a plane containing the axis Z, which line is referred to in the description below as the "generator" line. In other words, the property of the emitted light complies with a distribution relationship over the light-emitting surface that firstly possesses symmetry around the vertical axis of symmetry Z of the surface 6, and secondly presents a gradient along a generator line, i.e. along the curve constituted by the intersection of the light-emitting surface with a plane containing the vertical axis of symmetry Z.

In the preferred embodiment of the invention, the surface of axial symmetry is also a complete surface of revolution, such as a cylinder, or else a partial surface of revolution such as two cylinder portions separated along generator lines. Thus, when the light-emitting surface of axial symmetry is not a surface of revolution, it is still considered that the variation in the property of light takes place along a generator line of the surface.

When the surface is a surface of revolution, the property of the emitted light varies at all light-emitting points along the generator line of the light-emitting surface of revolution. As a result of this gradient, the property varies along the generator line passing through any point of the surface, and as a result, light coming from neighboring source points along said generator line on the surface does not have the same value for said property.

In another embodiment, the light-emitting surface of axial symmetry has a horizontal section that is polygonial, e.g. a section that is hexagonal, octagonal, etc. In this variant embodiment of the invention, the variation in the light property takes place along a generator line that is determined by the intersection between the light-emitting surface of symmetry and a plane containing the vertical axis of symmetry Z.

In the preferred embodiment of the invention, the property of light that varies is luminous exitance. In other words, the surface presents a gradient of luminous exitance I in a variation direction along a generator line of the light-emitting surface of axial symmetry.

In the embodiment shown in FIGS. 1 and 2, the light-emitting surface of axial symmetry is also a surface of revolution 6, in the form of a cylinder presenting a vertical axis of symmetry Z. The luminous exitance I varies between a point C and a point D along a direction that corresponds to a generator line of the cylinder 6 parallel to the vertical axis Z. Given the axial symmetry of the light-emitting surface 6, a generator line C' D' of the light-emitting surface is to be found diametrically opposite from the generator line C D of the light-emitting surface. In the variant embodiment shown in FIGS. 1 and 2, the light source 5 has a lighting ring 8 illuminating the top end of a cylindrical diffuser forming the light-emitting surface of axial symmetry 6. The lighting ring 8 has one or more light sources of any type enabling illumination to vary from the top end to the bottom end of the diffuser. By lighting a diffuser in part, e.g. in the neighborhood of one of its ends by means of a ring of light, said ring presenting an emission cone, the variation in the luminous exitance I results from the varying illumination of the diffuser and/or from diffusion by the diffuser.

Naturally, the surface 6 of axial symmetry may be other than a cylinder. In the examples shown in FIGS. 8, 9, and 10, the light-emitting surface 6 of axial symmetry is respectively a truncated cone, a hemisphere, and a disk. The generator lines C D and C' D' that are symmetrically opposite about the vertical axis of symmetry Z are shown diagrammatically in the drawings.

Figure 8:
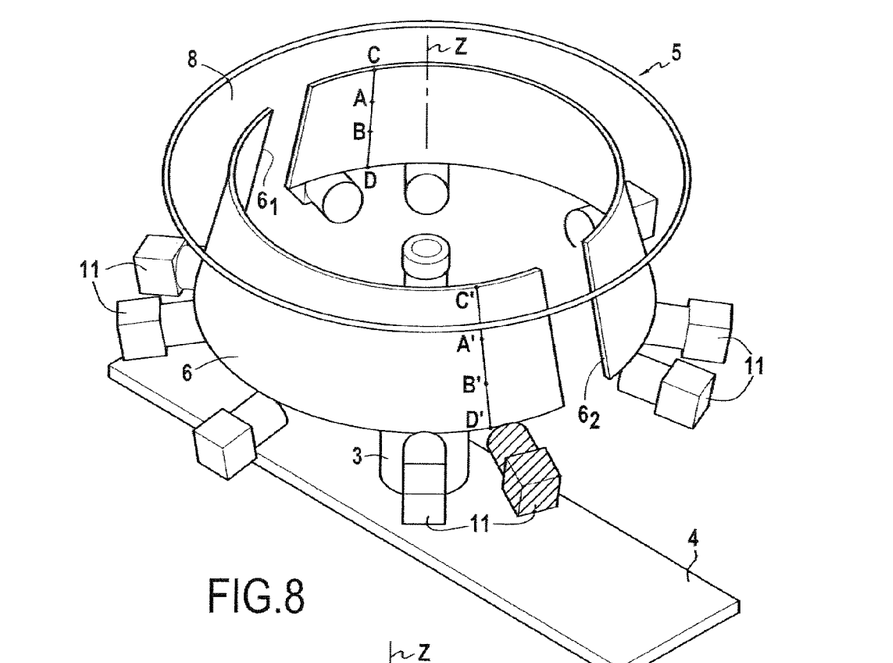
FIG. 8 shows another embodiment of a light source using a light-emitting surface of axial symmetry of the frustoconical type.

In the example shown in FIG. 8, the light-emitting surface 6 of axial symmetry comprises two truncated cone portions that are separated along generator lines of the truncated cone from which said portions are taken. The variation in the property of light takes place along generator lines of the truncated cone portions, i.e. along the curve constituted by the intersection between the truncated cone portions and a plane containing the vertical axis Z. The luminous exitance I varies along a direction that corresponds to a generator line of the truncated cone 6 between the points C and D. In the embodiment shown in FIG. 8, the two truncated cone portions thus occupy a truncated cone that may be considered as being discontinuous. Naturally, provision may be made for the light-emitting surface 6 of axial symmetry to be a surface of revolution that is complete or continuous, with a base that is preferably circular, and having an axis of symmetry Z that is vertical. In the variant embodiment shown in FIG. 8, the light source 5 has a lighting ring 8 illuminating the top end of a frustoconical diffuser forming the light-emitting surface 6 of axial symmetry.

Figure 9:
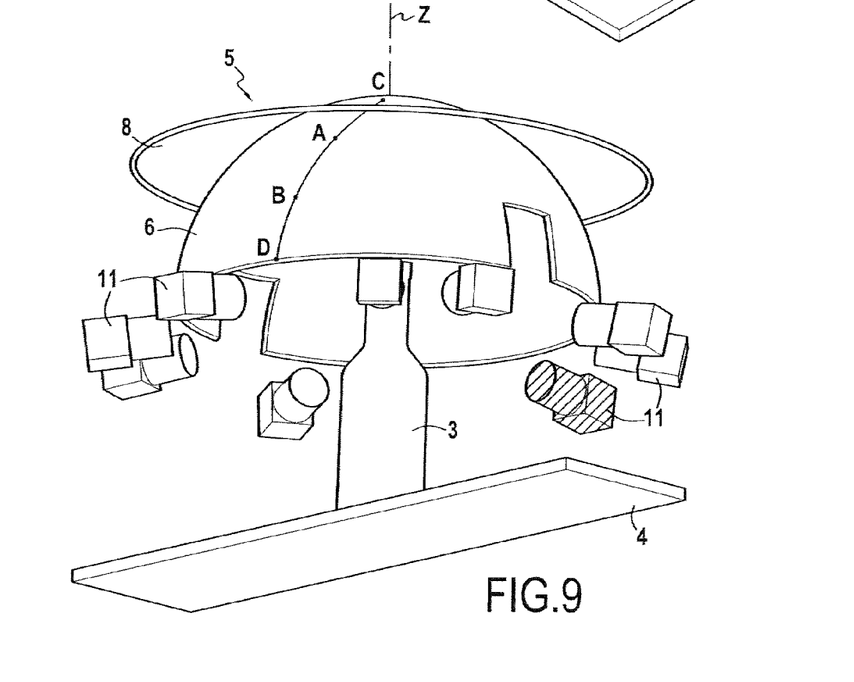
FIG. 9 shows another variant embodiment of the light source comprising a light-emitting surface of axial symmetry of the hemispherical type.

In the embodiment shown in FIG. 9, the light-emitting surface 6 of axial symmetry is likewise a surface of revolution, being hemispherical with a vertical axis of symmetry Z. Luminous exitance I varies along a direction that corresponds to a generator line of the hemisphere 6 between the points C and D. In the variant embodiment shown, the light source 5 comprises a lighting ring 8 illuminating a light diffusing hemisphere forming the light-emitting surface 6 of axial symmetry, the hemisphere being illuminated at a position remote from its equatorial plane.

Figure 10:
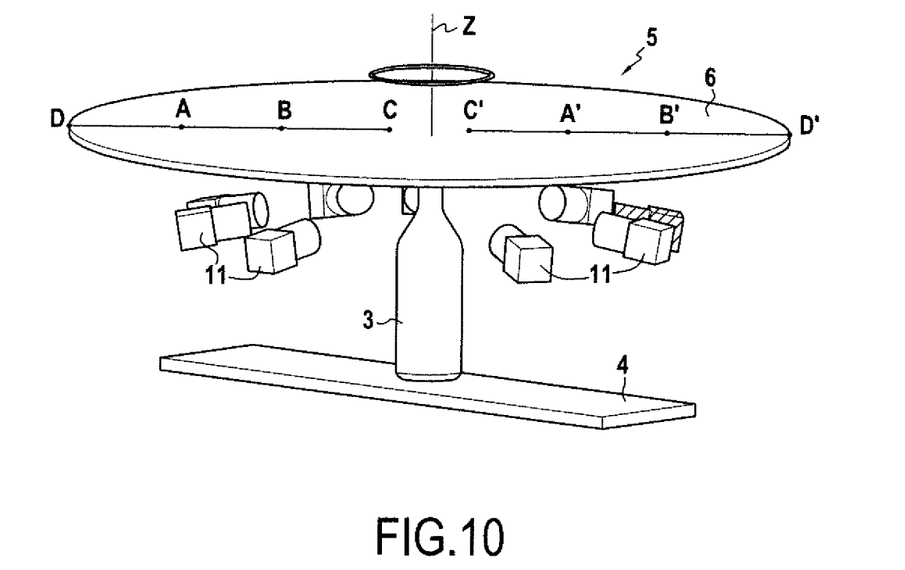
FIG. 10 shows another variant embodiment of a light source having a plane diffusion disk.

In the variant embodiment shown in FIG. 10, the light source 5 comprises a plane diffuser, such as a disk, forming the light-emitting surface 6 of axial symmetry with a vertical axis of symmetry Z. The diffuser disk is illuminated by illuminating lighting 8 either at its periphery or else at its center, as shown in the drawing. Luminous exitance I varies along the generator lines between points C and D, i.e. along the radii of the disk 6.

In the above-described examples, the gradient of luminous exitance I is obtained using illumination that varies along a given direction of a body that serves to diffuse light. Naturally, the gradient of luminous exitance I could be obtained in some other way.

More generally, the variation in the property of the light, e.g. the gradient of color or of luminous exitance I, may be produced by a tint applied to the surface or in the bulk of the luminous diffusing surface 6 of the source or by placing a transmission filter of varying spectrum in front of the diffusing light-emitting surface.

It should be observed that if consideration is given to any generator line of the surface, the particular function describing the variation in the property of the light that is used may take various shapes between the points C and D.

Figure 3A:
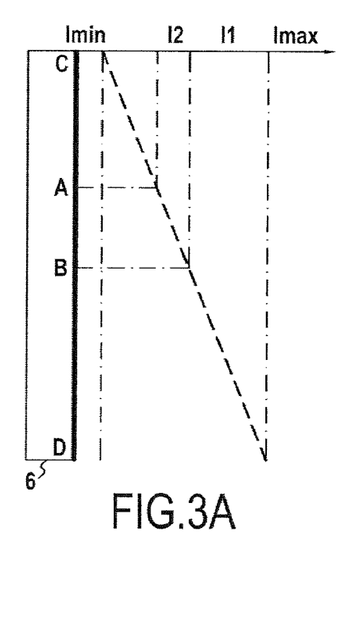
FIGS. 3A and 3B show embodiments of a light source presenting respective luminous exitance gradients, one that is constant and not zero, and another that varies monotonically, following a polynomial curve.
Figure 3B:
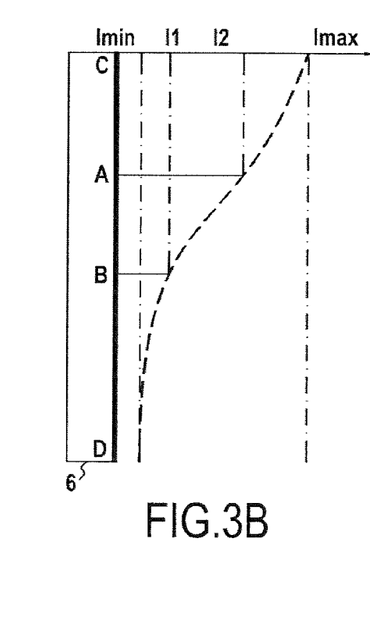

Preferably, in order to guarantee that variation is maintained along a generator line at any point of the surface, the variation is continuous and monotonic between the points C and D. As shown by way of example in FIGS. 3, 3A, and 3B, the variation in the luminous exitance may either take place along a constant positive gradient (FIG. 3), along a constant negative gradient (FIG. 3A), or along a portion of a continuous polynomial function (FIG. 3B).

According to a characteristic of the invention, the light-emitting surface 6 of axial symmetry is positioned to illuminate the outside of the container 3, and in particular the outside surface of the container that is to be observed and that might contain optical singularities 2. The light-emitting surface 6 of axial symmetry is positioned so that the vertical axis Z is perpendicular to and substantially intersects the travel direction f of the containers, while nevertheless not impeding movement of the containers.

According to an embodiment characteristic, the light source 5 is provided with an entry passage $6_1$ and an exit passage $6_2$ for a portion of a container, which passages are arranged symmetrically relative to the vertical axis Z. Thus, and as can be seen more particularly for the variant embodiments shown in FIGS. 1, 8, and 9, the light-emitting surface 6 of axial symmetry is provided with entry and exit passages $6_1$ and $6_2$ in the form of two cutouts of shape adapted to the corresponding portion of the container that passes through them. In order to observe the necks or the shoulders of containers, the entry and exit passages $6_1$, $6_2$ are adapted to pass the necks of containers in part or in full. In the example shown in FIG. 8, the entry and exit passages $6_1$, $6_2$ subdivide the light-emitting surface 6 of axial symmetry into two portions. Naturally, such entry and exit passages $6_1$, $6_2$ that open out into the two ends of the light-emitting surface may be provided in the variant shown in FIGS. 1 and 9. When a light-emitting surface 6 of axial symmetry is made in the form of a disk, the disk extends immediately above the mouths of the containers. When observing the insweep of the containers 3, the light source 5 is arranged in symmetrically inverted manner relative to the top and the bottom of the container.

The device 1 of the invention also has at least one image acquisition device 11, and in the example shown in FIGS. 1, 8, 9, and 10 a plurality of them, for the purpose of acquiring at least one view of a portion of the container 3 that might contain optical singularities as observed from at least one viewpoint P along an observation axis X. Conventionally, each image acquisition device 11 comprises a matrix camera with a lens. The image acquisition devices 11 are connected to means for processing at least one and in general manner a plurality of views that have been taken in order to analyze any optical singularities that might be present.

Thus, the view processor means analyze marks as optical singularities and interprets them in order to obtain information about the container or its fabrication for at least one operation selected from sorting, tracing, identifying, dating, or authenticating the container. For example, such optical singularities may be codes etched by laser onto the containers and in particular onto their necks. In another example application, such optical singularities may be identification marks or patterns carried by the containers. In another application, the optical singularities are refracting defects presented by the containers 3.

In the invention, as a result of the symmetry of the light-emitting surface around the vertical axes of symmetry Z, which substantially coincides in general with the axis of symmetry S of the containers, so that any portion illuminating one side of the container is situated diametrically opposite, about the axis Z, and generally about the axis of symmetry S, from another portion of the light-emitting surface presenting intensity that is substantially identical.

This makes it possible from a given viewpoint P and in a given observation direction X to receive both light transmitted through the container from an opposite portion of the source, and also light coming from a portion of the source situated on the same side as the container and reflected on the wall of the container.

FIG. 3 is a section in a plane containing the axis of symmetry Z of the source 5 and the observation direction X, and it serves to show the principle whereby light rays are collected so as to enable optical singularities 2 to be detected. The property of the light varies between two points C and D of the source portion opposite from the viewpoint P relative to the container. In the preferred variant, in which the source presents a gradient of luminous exitance, the luminous exitance I between the points C and D of the source varies between extreme values Imin and Imax. The light ray emitted by the light-emitting surface 6 from the point A is deflected by the optical singularity 2 that presents refracting power. This light ray coming from the point A of the light-emitting surface having luminous exitance equal to I1 is collected by the lens of the camera 11. The light ray emitted by the light-emitting surface 6 of axial symmetry from the point B passes in the immediate neighborhood of the optical singularity 2 without being deflected and is subsequently collected by the lens of the camera so as to reach the sensor of the camera in the neighborhood of the point collecting the light ray coming from the point A. This light ray is emitted by the light-emitting surface 6 of axial symmetry from point B having luminous exitance value equal to l2. Insofar as the light-emitting surface 6 of axial symmetry possesses a luminous exitance gradient along a generator line passing through the point A and the point B, the luminous exitance values l1 and l2 differ corresponding to the distance between the points A and B, and thus the luminous exitance values l1 and l2 differ increasingly with increasing strength of the deviation resulting from an optical singularity 2, such that in the image, remarkable contrast is observed at the location of the optical singularity, said contrast increasing with the refracting power of optical singularities. The processor means associated with the camera are adapted to detect these contrasts and to analyze them in order to recognize or identify the optical singularities corresponding thereto. It should be observed that if the light source did not possess a gradient of luminous exitance, then the luminous exitance values l1 and l2 would be equal, so there would be no contrast generated at the location of the optical singularity, thus preventing it being detected.

When the property of the light that varies between C and D is the color of the source, then the camera is a color camera. In this embodiment, the colors of the light emitted by the points A and B differ, and the processor means associated with the color camera are adapted to detect color contrasts or differences. The term "variation" of color is used to mean a variation that can be perceived by the camera 11 in the spectral composition of the light it detects.

In this variant embodiment, color varies progressively between the points C and D, e.g. from red to blue. By way of example, this result can be obtained by using a multicolor filter, or by using light emitting diodes (LEDs) of different colors that are positioned, pointed, and controlled in voltage, current, and/or pulse duration, so that the color that is perceived varies between the points C and D.

According to a characteristic of the invention, the method operates in a manner adapted to the optical transmittance of the containers 3. Thus, the containers 3 are considered as having high transmittance if, when using acquisition systems 11 to observe the optical singularities 2 and the outside surface of the container while they are being subjected to incident lighting in reflection, interfering spots appear in the image so as to interfere with the observation of the optical singularities, which spots are generated by interfering light rays propagating through the walls of the containers without attenuation. By way of example, these interfering spots may come from a reflection of the light source in the container, from a reflection of the light source on the inside surface of the container, from a reflection on the inside surface of the container of the image of the optical singularities to be observed, etc.

Figure 6:
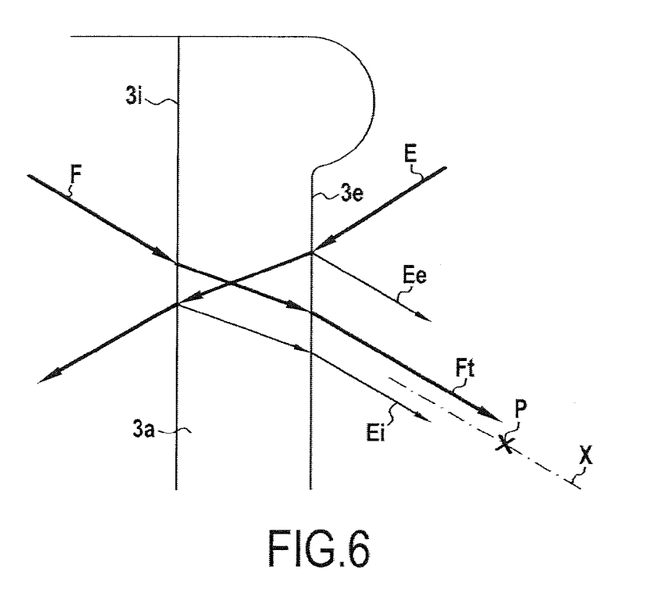
FIGS. 6 and 7 are diagrams showing the paths followed by light rays for containers presenting respectively high transmittance and low transmittance.

FIG. 6 shows a portion of a wall 3a of the container 3 that is defined by an inside surface 3i and by an outside surface 3e. For simplification purposes, the other wall of the container, through which the transmitted rays F have passed, is not shown. The light rays reaching the portion C D of the light-emitting surface after passing through the first wall are referenced F, whereas the light rays coming from the symmetrically opposite portion C' D' of the light-emitting surface are referenced E. For a container presenting high transmittance, the light rays E (coming from the portion C' D' of the light-emitting surface) illuminating the outside surface 3e lead to the appearance of light rays Ee that are reflected by the outside surface 3e, and light rays Ei that are reflected by the inside surface 3i. Because of the high transmittance of the container, the rays Ei reflected by the inside surface 3i are little attenuated by the material of the container and can therefore constitute interfering reflections associated with light energy that is not negligible compared with the light energy associated with the rays Ee reflected by the outside surface 3e and conveying information about the optical singularities. Consequently, in the resulting image, the energy transported by the interfering light rays Ei can impede the analysis of the light rays Ee, and consequently the analysis of an optical singularity 2, if any. More particularly, because of the high transmittance of the container, the optical singularities 2 of the outside surface 3e are reflected on the inside surface 3i, thereby causing interfering image duplication that disturbs the analysis of optical singularities, and this is particularly troublesome when the light rays Ei reflected by the inside surface 3i mix with the light rays Ee as reflected by the outside surface 3e and corresponding to an optical singularity 2. Nevertheless, the light rays Ft that have passed through the container 3 and that come from rays F emitted by the portion C D of the luminous structure 6 reach the viewpoint P while being absorbed little or not at all given the high transmittance nature of the container. Furthermore, the reflected light rays Ee and Ei are negligible compared with the intensity of the transmitted light rays Ft, such that the image obtained from the transmitted light has few or no interfering spots.

Figure 7:
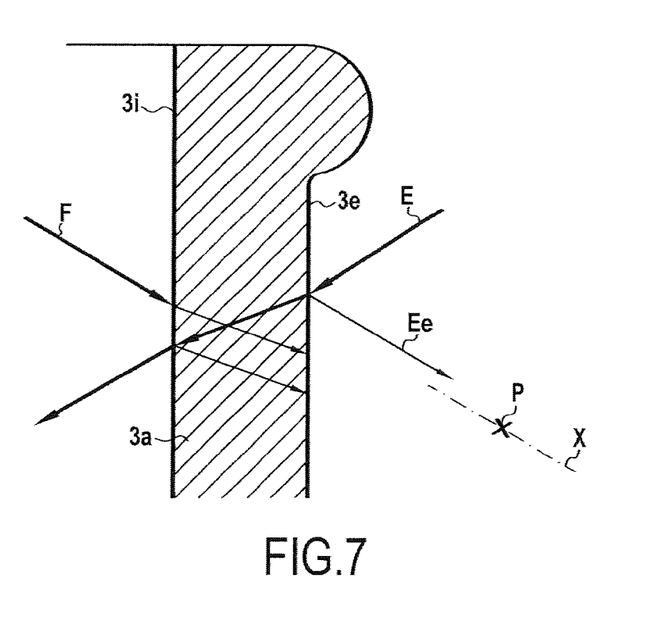

Containers 3 of low transmittance are containers where the interfering light rays are absorbed by the tint of the material to such an extent that they do not disturb the analysis of optical singularities. This can be observed when the interfering reflections from the light source in the container are absorbed by the tint of the material to such an extent that they do not disturb the analysis of optical singularities 2. As shown in FIG. 7, because of the low transmittance of the container, the light rays E of the illumination emitted from the portion C' D' are attenuated on passing through the wall 3a of the container to an extent that is sufficient for their remaining light energy on reaching the image acquisition device 11 to be too low to form a duplication of the optical singularity 2 in the view. (The rays Ei reflected by the inside surface 3i are of negligible intensity). The image acquisition device 11 thus recovers only the light rays Ee reflected by the outside surface 3e. Likewise, the rays F emitted by the portion C D of the light-emitting surface are absorbed by the walls of the container, given the low transmittance nature of the container. Furthermore, because of the low transmittance of the container, the rays from the illumination that penetrate the material are attenuated on passing through the walls of the container to an extent that is sufficient for their light intensity to be too low to form duplication of the optical singularity in the view.

Naturally, the high and low transmittance quality should be considered relative to the spectral composition of the light in question and thus the light emitted by the light source 5.

With high transmittance containers 3, the image acquisition device 11 is positioned and/or adjusted in such a manner as to make a view of the portion of the container from the viewpoint P that receives the light beams coming from a portion of the light-emitting surface of axial symmetry that is diametrically opposite relative to the container 3, and that are transmitted through the walls of the container in accordance with the laws of refraction. As can be seen clearly in FIG. 4, which shows a transmission mode of operation, the image acquisition device 11 is positioned and/or adjusted to recover the light beams F coming from the light-emitting surface 6 of axial symmetry that have passed through the container 3, such as the beams coming from the points A and B situated between the extremes C and D. Relative to the container 3 the viewpoint P is diametrically opposite from the portion of the light-emitting surface 6 of axial symmetry that generates the light it observes looking along the observation direction X.

Figure 4:
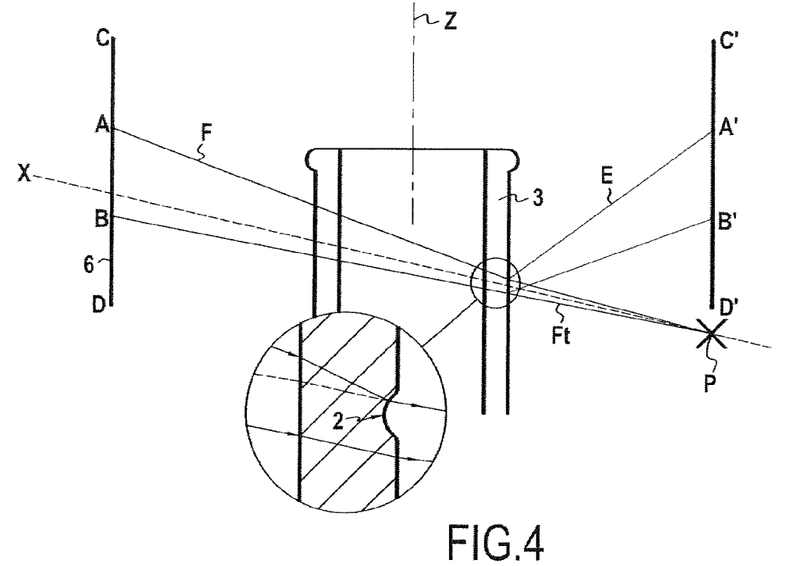
FIG. 4 is a diagram showing the principles of operation of the invention in transmission mode.

According to the invention, and because of the axial symmetry of the source, a diametrically opposite luminous portion C' D' is to be found opposite the portion C D. As shown in FIG. 4, looking from the viewpoint P along the observation direction X also makes it possible to receive light rays coming from the portion of the light-emitting surface 6 that is situated on the same side as the viewpoint P relative to the axis of symmetry, i.e. from the source portion C' D', after they have been reflected on the wall of the article. Nevertheless, the rays coming from the points A', B' and that are reflected on the wall of the container possess a level of energy that is negligible compared with the rays coming from the points A and B and that have been transmitted through the container.

Figure 5:
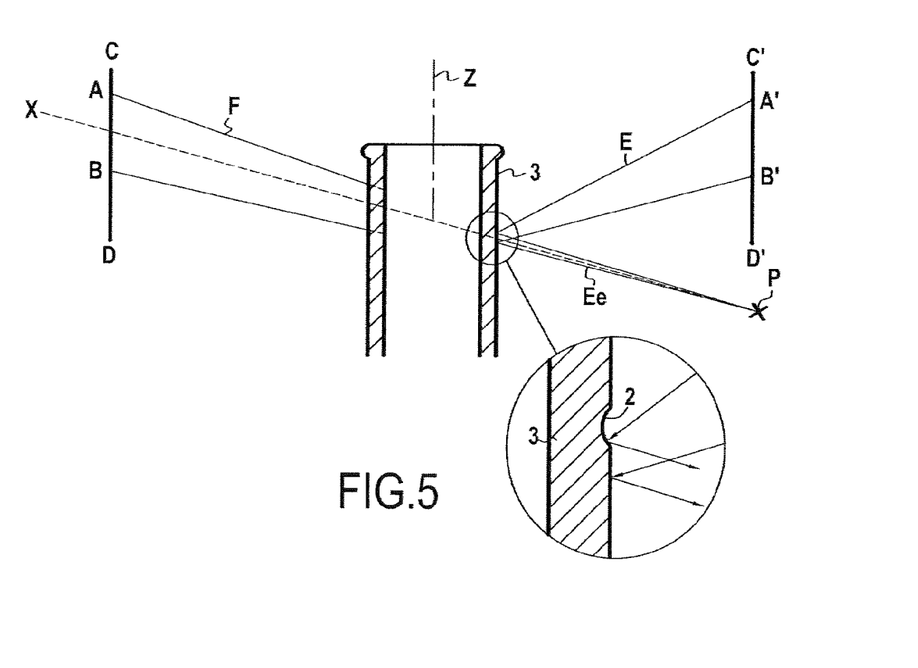
FIG. 5 is a diagram explaining the principle of operation of the invention for a mode of operation in reflection.

With containers of low transmittance, the image acquisition device 11 takes a view of the portion of the container 3 from the viewpoint P and looking along the observation direction X by receiving the light beams that come from a portion C' D' of the light-emitting surface 6 of axial symmetry that is situated on the same side of the container, which beams are reflected by the surface of the container in compliance with the laws of specular reflection. Thus, as can be seen more clearly in FIG. 5, which shows a reflection mode of operation, the image acquisition device 11 is positioned and/or adjusted to recover the light beams coming from the light-emitting surface 6 of axial symmetry that have been reflected by the container 3. FIG. 5 also shows that the light from the portion CD of the source that is opposite from the viewpoint P is absorbed by the low transmittance glass.

Naturally, the viewpoints P can be adjusted in height, and/or the observation directions X can be adjusted in angle relative to the vertical axis of symmetry Z depending on dimensions, and depending for example on the diameter of the observed portion of the container 3, and depending on whether the mode of operation is in transmission or in reflection.

The device 1 of the invention makes it possible to observe and analyze optical singularities regardless of the transmittance of containers 3.

In a variant embodiment, the emission spectrum of the light source 5 is adapted either to increase, or else to reduce or to eliminate, the energy of light beams transmitted through the walls 3a of the container. Since the high or low transmittance quality varies with the spectral composition of the light in question, and thus with the light emitted by the light source 5, it is possible to improve the quality of the images for the transmission or reflection mode of operation by adapting the emission spectrum of the light source 5 to the transmission spectrum of the container so as to increase or reduce or even eliminate the energy of light beams transmitted through the walls 3a of the container. Naturally, the sensitivity spectrum of the image acquisition device 11 must also be taken into account when performing such adaptation. In this variant, the emission spectrum of the light source 5 may be adapted, e.g. by using filters, but preferably by being electrically adjustable, e.g. by using controllable combinations of LEDs of different colors. In the transmission mode of operation, the emission spectrum of the light source 5 is adjusted or matched so as to increase the energy of the transmitted light beams Ft, these light beams thus acquiring energy that is considerably greater than the energy of the reflected beams Ee and Ei. In the reflection mode of operation, the emission spectrum of the light source 5 is adjusted or matched so as to reduce or even eliminate the energy of the transited light beams Ft and Ei, these beams thus acquiring energy that is negligible compared with the energy of the reflected beams Ee.

In a variant embodiment, the device 1 seeks to enable a plurality of views to be taken of the portion of the container 3 that might contain optical singularities 2 along various observation axes X distributed around the vertical axis Z of the container 3, which axes preferably intersect the axis Z, so as to provide complete or even redundant analysis of the periphery of the container. These views are obtained by means of a combination of cameras 11 and/or optical systems. In the example shown in FIGS. 1 and 2, the device 1 has ten cameras distributed around the light-emitting surface 6 of axial symmetry without impeding the travel of the containers 3. For example, the number of cameras 11 is less than or equal to the number of viewpoints P and of observation directions X.

It should be observed that the positions of the cameras 11 may correspond with the positions of the viewpoints P, but need not. In certain configurations, the acquisition devices 11 may include not only cameras, but also deflection optical systems enabling the cameras to be located in positions other than the viewpoints P. Advantageously, the deflection optical systems are adjustable so as to adjust the directions in which the observation axes X point and/or the positions of the viewpoints P. The deflector optical systems may be of any known type, e.g. combinations of mirrors and/or prisms. These devices also make it possible, should that be necessary, for the number of cameras 11 to be less than the number of viewpoints P and of observation directions X.

In order to analyze optical singularities 2 situated on the necks of containers 3, it is found to be advantageous to point the observation axes X upwards, either by acting on the cameras 11 or by using optical deflector systems, e.g. using an angle lying in the range 3° to 10° relative to the horizontal. In an advantageous configuration, the light source 5 situated above a plane that intersects the optical singularity 2, while the viewpoints P are situated beneath the plane.

In the above embodiments, all of the light-emitting surface 6 of axial symmetry is illuminated simultaneously. It should be observed that the light-emitting surface 6 of axial symmetry could be subdivided into angular sectors capable of being illuminated or switched off selectively. Thus, provision can be made to illuminate different angular portions of the light-emitting surface 6 of axial symmetry separately and in succession while acquiring views synchronously from viewpoints that are opposite from or on the same side as said angular portions. In general, the light source 5 may be controlled by any appropriate means in terms of light level and/or duration of illumination.

The device 1 of the invention makes it possible to perform a method of observing and analyzing optical singularities 2 carried at the surface or in the wall of a container 3.

In a variant embodiment, the container 3 may be caused to rotate while traveling past one or more cameras.

In a preferred variant embodiment, the method seeks to ensure that the containers travel without rotating about their axes of symmetry S along a direction of instantaneous translation perpendicular to and substantially intersecting the vertical axis Z of the light-emitting surface 6 of axial symmetry. In this preferred variant embodiment, the passages $6_1$ and $6_2$ for portions of the containers are arranged in the light-emitting surface of axial symmetry so as to allow the containers to travel along a determined path.

In particular, a device 1 of the invention that comprises a plurality of viewpoints P distributed around the container, with upwardly-directed observation directions X that intersect the vertical axis Z and that point towards the necks of containers, and having a light-emitting surface 6 of axial symmetry of vertical axis Z that presents monotonic variation along a generator line of the light property that is measurable by the image acquisition systems 11 is suitable, without modification, for operating equally well in reflection and/or transmission mode depending on the containers, for reading low contrast Datamatrix codes obtained by laser marking the necks of the containers, with this taking place in a single inspection station for containers traveling linearly.

The invention is not limited to the embodiments described and shown since various modifications can be made thereto without going beyond its ambit.

The invention claimed is:

1. An observation and analysis method for observing and analyzing optical singularities (2) that deflect light and that are carried at the surface or in the wall of a container (3) made of glass and possessing an axis of symmetry (S), the method consisting in:
   illuminating the container by means of a diffuse light source (5) presenting variation in a property of light along a variation direction;
   placing at least one image acquisition device sensitive to said property of light and to its variation to take at least one view of a container portion that might contain optical singularities when observed from at least one viewpoint (P) along an observation axis (X); and
   processing at least one view in order to analyze the optical singularities;
   the method being characterized in that it consists in:
   illuminating the outside (3e) of the container by using a light-emitting surface (6) of axial symmetry around a vertical axis (Z) parallel to the axis of symmetry (S) of the containers, with the variation direction of the light property running along a generator line of the light-emitting surface at all points of the light-emitting surface;
   with containers of low transmittance, taking the view of the container portion by the image acquisition device receiving light beams coming from a portion of the light-emitting surface (6) of axial symmetry situated on the same side of the container as the viewpoint (P), which beams are reflected by an outside surface of the container in application of the laws of specular reflection; or
   with containers of high transmittance, taking the view of the container portion by the image acquisition device receiving light beams coming from a portion of the light-emitting surface (6) of axial symmetry that is diametrically opposite from the viewpoint (P) relative to the container, which beams have been transmitted through the walls (3a) of the container in application of the laws of refraction.

2. An observation and analysis method according to claim 1, characterized in that it consists in considering that containers (3) have high transmittance when interfering spots appear in the image to interfere with the observation of optical singularities, where the spots are generated by interfering light rays propagating without attenuation through the wall, and in considering that containers (3) are of low transmittance when said interfering light rays are absorbed by the tint of the material to such an extent as to avoid disturbing the analysis of optical singularities.

3. An observation and analysis method according to claim 1, characterized in that it consists in causing containers (3) to travel, without rotating about their axes (S), along a travel direction (f) perpendicular to and substantially intersecting the vertical axis of symmetry (Z) of the light-emitting surface (6) of axial symmetry.

4. An observation and analysis method according to claim 3, characterized in that it consists in providing passages ($6_1$, $6_2$) in two opposite sides of the light-emitting surface (6) of axial symmetry for passing at least a portion of a traveling container.

5. An observation and analysis method according to claim 1, characterized in that it consists in taking a plurality of views of the portion of the container (3) that might contain optical singularities (2) along different observation axes (X) that are distributed angularly around the vertical axis of the container to ensure that the periphery of the container is analyzed completely or even redundantly.

6. An observation and analysis method according to claim 1, characterized in that it consists in taking a plurality of views obtained by means of a combination of cameras and optical systems so that the number of cameras is less than or equal to the number of viewpoints and of observation directions.

7. An observation and analysis method according to claim 1, characterized in that it consists in pointing the observation axes (X) upwards in order to analyze the optical singularities (2) situated on the necks ($3_1$) of the containers.

8. An observation and analysis method according to claim 1, characterized in that the analysis consists in analyzing marks as optical singularities (2) and in interpreting them in order to obtain information about the container or its fabrication for at least one operation selected from: sorting, tracing, identifying dating, and authenticating the container.

9. An observation and analysis method according to claim 1, characterized in that the analysis consists in detecting and/or identifying optical singularities as defects of the containers.

10. An observation and analysis method according to claim 1, characterized in that when observing a container, different angular portions of the light-emitting surface (6) of axial symmetry are illuminated separately and in succession while simultaneously acquiring views synchronously with the illumination of the angular portions, the views being taken from viewpoints that are opposite from or on the same side as said angular portions relative to the container (3).

11. An observation and analysis method according to claim 1, characterized in that it consists in illuminating with a diffuse light source (5) in which the light property that varies along a generator line of the light-emitting surface of axial symmetry is the luminous exitance of the light-emitting surface.

12. An observation and analysis method according to claim 1, characterized in that the light property that varies along a generator line of the light-emitting surface of axial symmetry is the color of the emitted light.

13. An observation and analysis method according to claim 1, characterized in that the emission spectrum of the light source (5) is adapted to increase or else reduce or even eliminate the energy of the light beams transmitted through the walls (3a) of the container.

14. A device for observing and analyzing optical singularities that deflects light and that are carried at the surface of or in the wall of a glass container (3) possessing an axis of symmetry (S), the device comprising:
- a diffuse light source (5) presenting variation of a property of light along a variation direction;
- at least one image acquisition device (11) for taking at least one view of a container portion that might contain optical singularities observed from at least one viewpoint (P) along an observation axis (X); and
- means for processing at least one view in order to analyze the singularities;

the device being characterized in that:
- a light-emitting surface is positioned to illuminate the outside of the container, said surface being a surface (6) of axial symmetry about a vertical axis (Z) parallel to the axes of symmetry (S) of the containers, with the light property varying along a generator line of the light-emitting surface along the variation direction at all points of the light-emitting surface of axial symmetry;
- for containers (3) of low transmittance, the image acquisition device (11) is suitable for taking the view of the container portion from a viewpoint (P) in order to receive the light beams coming from a portion of the light-emitting surface (6) of axial symmetry that is situated on the same side of the container as the viewpoint (P), which beams are reflected by an outside surface of the container; or
- for containers (3) of high transmittance, the image acquisition device is suitable for taking the view of the container portion from a viewpoint (P) for receiving light beams coming from a portion of the light-emitting surface (6) of axial symmetry that is diametrically opposite from the viewpoint (P) relative to the container, which beams are transmitted through the walls (3a) of the container.

15. A device according to claim 14, characterized in that the light-emitting surface (6) of axial symmetry is a surface of revolution.

16. A device according to claim 14, characterized in that the luminous exitance of the light-emitting surface (6) of axial symmetry varies at all points of the light-emitting surface of axial symmetry along a generator line of said surface.

17. A device according to claim 14, characterized in that the color of the light emitted by the light-emitting surface (6) of axial symmetry varies at all points of the light-emitting surface of axial symmetry along a generator line of said surface.

18. A device according to claim 14, characterized in that the light source (5) includes at least one lighting ring (8) illuminating the bottom or top end of a cylindrical or frustoconical diffuser.

19. A device according to claim 14, characterized in that the luminous source (6) of axial symmetry includes a lighting ring illuminating a light diffusing hemisphere opposite from its equatorial plane to vary a function of the point under consideration of the diffuser, but with axial symmetry relative to the axis of the hemisphere.

20. A device according to claim 14, characterized in that the light source (5) includes a plane diffuser disk illuminated at its center by a source or at its periphery by a lighting ring to vary a function of the point under consideration of the diffuser, but with axial symmetry relative to the axis of the disk.

21. A device according to claim 14, characterized in that the emission spectrum of the light source (5) is adapted to increase or else reduce or even eliminate the energy of light beams transmitted through the walls (3a) of the container.

22. A device according to claim 14, characterized in that the light source (5) includes a diffuser that is completely illuminated and against which there is placed on one side or the other a film of transmission that varies, at least for one wavelength, along a generator line of the light-emitting surface.

23. A device according to claim 14, characterized in that the light-emitting surface (6) of axial symmetry has a plurality of angular sectors that are controlled to be switched on and/or off selectively.

24. A device according to claim 14, characterized in that the light-emitting surface (6) of axial symmetry is provided with an entry passage ($6_1$) and an exit passage ($6_2$) for a portion of a container, which passages are arranged symmetrically about the vertical axis (Z).

25. A device according to claim 14, characterized in that it includes a series of image acquisition devices (11) placed around the vertical axis in order to observe the container from a plurality of viewpoints enabling all or part of the periphery of the container to be observed.

26. A device according to claim 14, characterized in that the image acquisition devices (11) are positioned with an observation axis (X) pointing upwards at an angle lying in the range 3° to 10° relative to the horizontal.

* * * * *